United States Patent [19]
Lafontaine

[11] Patent Number: 5,702,413
[45] Date of Patent: Dec. 30, 1997

[54] CURVED BRISTLE ATHERECTOMY DEVICE AND METHOD

[75] Inventor: Daniel M. Lafontaine, Plymouth, Minn.

[73] Assignee: Scimed Life Systems, Inc., Maple Grove, Minn.

[21] Appl. No.: 584,474

[22] Filed: Jan. 11, 1996

[51] Int. Cl.[6] .................... A61B 17/22; A61M 29/00
[52] U.S. Cl. ................................ 606/159; 606/191
[58] Field of Search ........................ 606/159, 170, 606/191, 192, 194, 70; 604/22; 128/751

[56] References Cited

U.S. PATENT DOCUMENTS

| | | | |
|---|---|---|---|
| 1,975,673 | 5/1934 | Sayre | 606/159 X |
| 2,701,559 | 2/1955 | Cooper . | |
| 3,074,396 | 1/1963 | MacLean . | |
| 3,550,223 | 12/1970 | Erb . | |
| 3,687,129 | 8/1972 | Nuwayser . | |
| 4,108,162 | 8/1978 | Chikashige et al. . | |
| 4,235,244 | 11/1980 | Abele et al. . | |
| 4,271,845 | 6/1981 | Chikashige et al. . | |
| 4,361,948 | 12/1982 | Omata . | |
| 4,465,072 | 8/1984 | Taheri et al. | 606/159 |
| 4,850,957 | 7/1989 | Summers | 604/22 |
| 4,936,312 | 6/1990 | Tsukagoshi et al. . | |
| 4,994,067 | 2/1991 | Summers | 606/159 |
| 5,047,040 | 9/1991 | Simpson et al. | 604/22 X |
| 5,152,744 | 10/1992 | Krause et al. | 604/22 |
| 5,240,675 | 8/1993 | Wilk et al. | 604/22 X |
| 5,364,473 | 11/1994 | Bowman | 606/159 X |
| 5,370,653 | 12/1994 | Cragg . | |
| 5,402,790 | 4/1995 | Jang et al. | 606/159 X |
| 5,474,075 | 12/1995 | Goldberg et al. . | |
| 5,527,325 | 6/1996 | Conley et al. | 606/159 |
| 5,535,756 | 7/1996 | Parasher . | |
| 5,554,163 | 9/1996 | Shturman | 604/22 |

FOREIGN PATENT DOCUMENTS

| | | | |
|---|---|---|---|
| 8150204 | 6/1996 | Japan . | |
| 8154893 | 6/1996 | Japan . | |
| 0095459 | 4/1939 | Sweden | 606/159 |
| 94021177 | 9/1994 | WIPO | 606/159 |

OTHER PUBLICATIONS

4–pg. brochure re. ESB™ Esophagael Specimen Brush, Microvasive® Boston Scientific Corporation, 1993.
2–pg. brochure re. Cytology Brushes, Microvasive® Boston Scientific Corporation, 1993.

*Primary Examiner*—Michael Buiz
*Assistant Examiner*—Nancy Connolly Mulcare
*Attorney, Agent, or Firm*—Robert E. Atkinson

[57] ABSTRACT

An medical device with hook like bristles suitable for capturing occlusive material. The device is inserted to a patient's vasculature and moved through an area of occlusion in such a way as to dislodge and capture the material causing the occlusion.

13 Claims, 7 Drawing Sheets

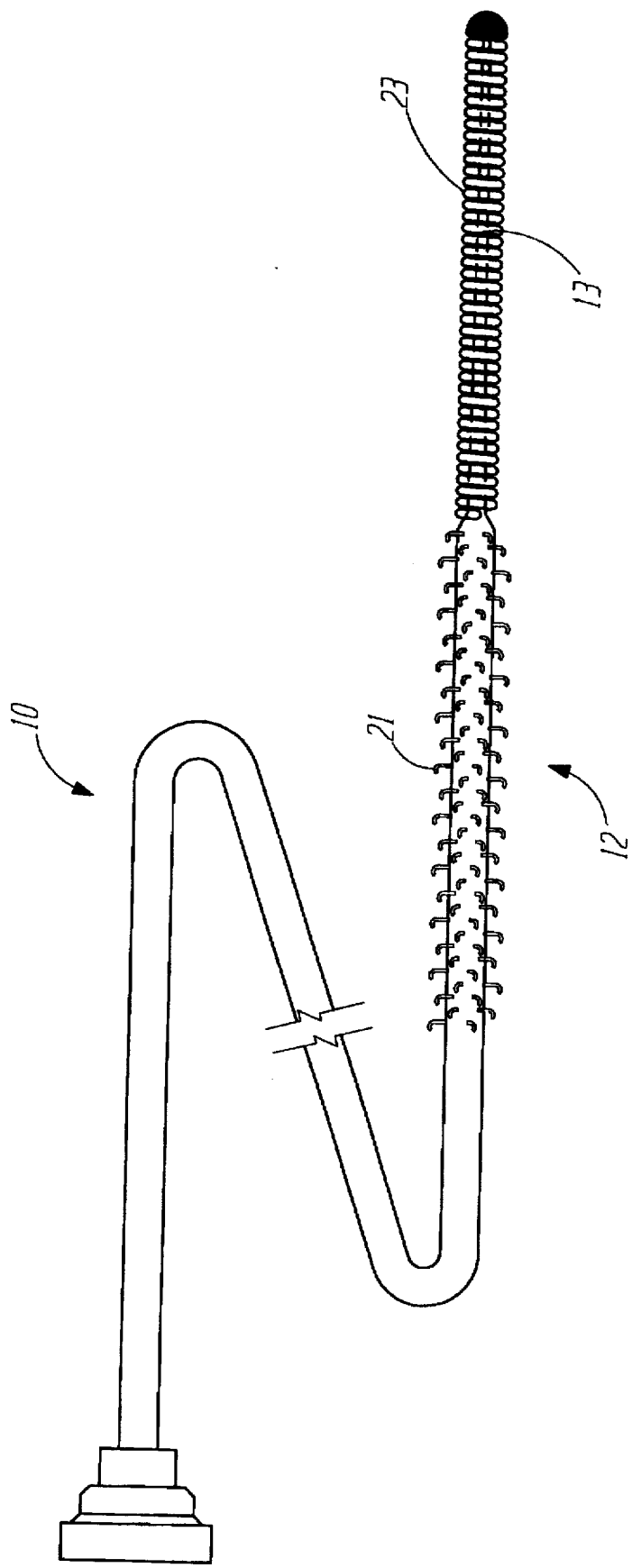

CURVED BRISTLE ATHERECTOMY DEVICE AND METHOD

FIELD OF THE INVENTION

The present invention generally relates to minimally invasive devices used for the removal and collection of material from within human beings. More specifically, the present invention relates to vascular devices utilizing bristles to extract occlusive material and methods of use thereof. Those skilled in the art will recognize the benefits of applying the present invention to similar fields not discussed herein.

BACKGROUND OF THE INVENTION

A wide variety of therapeutic techniques have been developed to correct or inhibit vascular diseases. Coronary artery disease (CAD), for example, is an adverse condition of the heart in which the blood flow to the heart muscle is partially or totally restricted by occlusive material in the coronary arteries that narrows the blood flow lumen. The occlusive materials deprive portions of the heart muscle of essential oxygenated blood.

CAD may be treated by a surgical technique referred to as coronary artery bypass graft (CAB) surgery. This surgical procedure involves supplementing blood flow to the heart muscle by grafting non-native conduit such as a saphenous vein graft (SVG) to the heart. A first end of the SVG is connected to the ascending aorta (proximal to the occlusive material) and the other end is connected to the artery distal of the occlusive material. Although this technique has been useful for treating CAD in native coronary arteries, it is not uncommon for occlusive material to form over time in the SVG thereby necessitating additional therapy. Typically, the nature of the occlusive material in the new SVG may be diffuse, friable, grumous-like, paste-like, granular, and/or chunky.

Percutaneous translumenal coronary angioplasty (PTCA) has gained wide acceptance as an effective and less invasive alternative to CAB surgery in certain patient groups. The PTCA procedure involves the use of an angioplasty balloon catheter, several types of which are well known in the art. The balloon catheter is inserted into the body via the femoral artery and navigated to the coronary arteries assisted by a guide catheter and (usually) a guide wire. The balloon is positioned across the restriction in the artery and subsequently inflated. The inflated balloon widens the restriction and restores blood flow to portions of the heart muscle previously deprived of oxygenated blood.

Although balloon PTCA has been demonstrated to be clinically effective in treating a wide variety of vascular restrictions, there are alternative devices and techniques which are specially adapted to treat lesions with complex morphology and/or unique pathology. For example, SVGs commonly contain abnormal deposits which are diffuse, degenerated, and thrombus—containing. Because treating SVG lesions with balloon PTCA has an unfavorably high incidence of distal embolization, alternative therapies such as atherectomy have been favored.

Atherectomy (or thrombectomy) is an alternative to balloon PTCA and targets specific types of lesion morphology and pathology. Atherectomy, as distinguished from balloon PTCA, removes the occlusive material from the local vasculature rather than molding or reshaping the restriction by compression. While some prior are atherectomy devices have been specifically indicated to be effective for treating certain types of diseased SVGs, the incidence of complications (e.g. distal coronary artery embolization, cerebral embolization via the aorta) has been reported to be suboptimally high. Thus, there is a need for an improved atherectomy or thrombectomy device for the removal occlusive material, particularly in friable, diffusely diseased SVGs.

One type of atherectomy/thrombectomy device is a brush like device as described in U.S. Pat. No. 5,370,653 to Cragg. The Cragg patent teaches a device that dislodges intravascular material but does not capture it, thereby allowing the dislodged material to travel through the vasculature and potentially cause blockage elsewhere. Heretofore attempted remedies to this problem have included placing a downstream filter to capture the dislodged particles or administering clot dissolving drugs during the procedure. While these remedies can be effective, they obviously involve additional devices and procedures that have a corresponding additional cost. Thus, an atherectomy thrombectomy device that captures the dislodged material would be advantageous.

SUMMARY OF THE INVENTION

The present invention overcomes the deficiencies of the prior art by providing an atherectomy/thrombectomy device that dislodges and captures material removed from a patient's vasculature and a method of using the atherectomy/thrombectomy device. In one embodiment of the invention, the device includes an elongate shaft with a distal end having curved bristles suited for dislodging and capturing occluding material. The shaft may further include a spring tip on its distal end.

In use, the device is inserted into a patient's vasculature and advanced to a point adjacent the area to be treated. The bristles are then moved through the area to be treated in such a way as to dislodge and capture occlusive material in the bristles. Finally the device is removed from the patient's body.

In another embodiment of the invention, the device may also include a sheath. The sheath is moveable, relative to the bristles, such that it can cover and protect the bristles or be retracted to expose the bristles. Use of this embodiment also requires inserting the device into a patient's vasculature and advancing it to a point adjacent the area to be treated. The bristles are then exposed to the occlusive material by retracting the sheath. Similar to the previous embodiment, the bristles are moved through the area to be treated. After the occlusive material is dislodged and captured by the bristles, the entire device is removed from the patient.

Another embodiment of the invention is a catheter with an inflatable balloon near its distal end and curved bristles located proximal to the balloon. The catheter includes a first lumen for use in inflating the balloon. The catheter may also include a second lumen for transporting a flushing fluid to the bristles which surround the catheter proximal to the balloon. This embodiment may also include a sheath, which can cover the bristles during flushing or while the catheter is moved within the patient's vasculature.

Use of the device of this embodiment is similar to that described above, in that the bristles dislodge and capture occlusive material. However, it is also possible to clean the bristles while the catheter is in the patient's body. In-vivo cleaning is accomplished by moving the sheath forward to cover the bristles and then inflating the balloon to seal the bristles between the sheath and the balloon. Fluid is then flushed through a tube inside the catheter. The tube directs flushing fluid to holes near the bristles. The flushing fluid cleans any material from the bristles and transports that material out of the patient's body via the space between the sheath and the catheter.

BRIEF DESCRIPTION OF THE DRAWINGS

These and other objects, advantages, and features of the invention will become apparent from the following detailed description of the preferred embodiments of the invention, in which:

FIG. 1a is a side view of a first embodiment of the invention.

DETAILED DESCRIPTION OF THE INVENTION

Figure 1B:
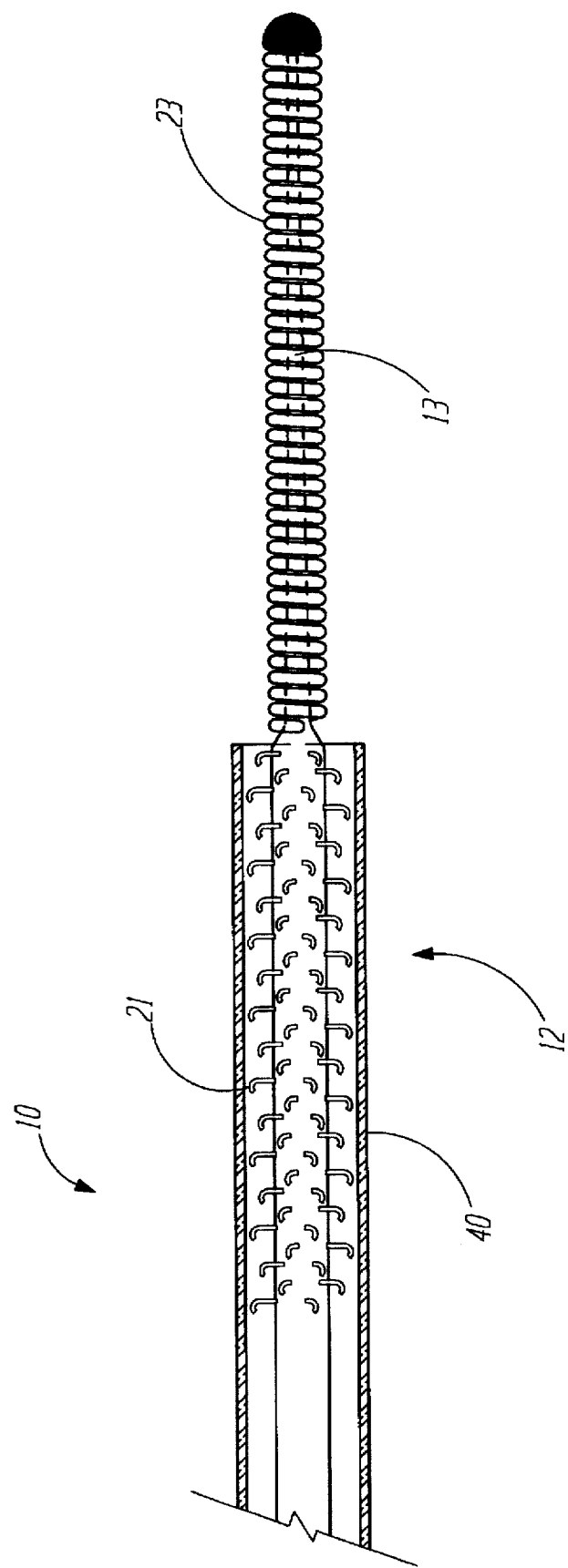
FIG. 1b is a side view of a modification of the embodiment of FIG. 1a which includes a sheath.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions, and manufacturing process are provided for selected elements. All other elements employ that which is known to those skilled in the field of the invention. Those skilled in the art will recognize that many of the examples provided have suitable alternatives that may also be utilized.

The embodiments described below describe the invention as a guide wire or balloon catheter. However, those skilled in the art will recognize that this invention may be used in a variety of intralumenal devices including, but not limited to, catheters, exfoliators, cell collectors, basket retrieval devices, urinary devices, and intestinal devices.

A device according to the present invention includes an elongate body with a proximal and a distal end having curved bristles proximate to the distal end. As shown in FIG. 1a, the elongate body can be a shaft 10.

Shaft 10 can be made of stainless steel, nitinol, or other suitable medical Wade alloys. Shaft 10 is cold drawn, straightened, and then ground to about 0.010–0.020" in diameter but preferably in the range of 0.014–0.018" in diameter. The shaft 10 may be either standard guide wire length, about 150–175 cm, or standard exchangeable guide wire length, about 300 cm.

Curved bristles 21 are then attached proximate to the distal end of shaft 10. Bristles 21 need to be atraumatic, so as not to grab fatty or muscular tissue, but have the ability to hold fibrous tissue, such as fibrin in thrombus or collagen in connective tissue. Accordingly, bristles 21 can be made of a variety of materials including suitable medical Wade polymers, shape memory polymers, shape memory alloys (e.g., Nitinol™), and medical grade radio-opaque alloys. Bristles 21 may be 1.0–4.5 mm in length and can cover an area of 2–8 cm. Bristles 21 may be hook shaped and may be biased in a distal facing or proximal facing orientation but are preferentially biased radially.

In addition to the many materials available to make bristles 21, there are a variety of manufacturing methods. These methods include, but are not limited to, the following:

1. Stitching loops into a polymer sleeve, that surrounds the shaft proximate of the distal end, and then severing the loops in such a way as to leave curved bristles and stubble.

2. Extruding elastomer over the shaft, proximate of the distal end, and then pressure molding the extrudate to make spikes that stick radially from the shaft. These spikes are then thermally rolled into hooks and biased in any desired direction.

3. Winding loops of wire around the shaft, proximate of the distal end, and lashing the loops down with fine wire. A portion of these loops is then removed, leaving curved bristles and no stubble.

4. Wrapping individual coils around the shaft, proximate of the distal end, leaving each end of the coil extending axially. The ends of these coils are then rolled over into hooks and biased in any desired direction.

The distal end of shaft 10 is further ground to form a tapered distal segment 13 tapering from the proximal to the distal end of distal segment 13. Distal segment 13 may further be stamped to form a rectangular safety ribbon. Distal segment 13 may include a radio-opaque coil 23, made of a platinum-iridium alloy or other suitable medical grade radio-opaque alloy, to make the distal segment of shaft 10 more visible under fluoroscopy. Coil 23 has a diameter of about 0.010–0.020" and encircles distal segment 13 along its entire length. Coil 23 is attached to shaft 10 by soldering the proximal portion of coil 23 to the proximal portion of distal segment 13 and welding the distal portion of coil 23 to the distal end of distal segment 13, thereby forming an atraumatic tip.

In use, shaft 10 is inserted into a human's vasculature and advanced to a site to be treated. Once the bristles 21 are adjacent the site to be treated, the bristles 21 are rubbed against the lesion in any way that will cause material to be dislodged from the interior of the vessel. Possible rubbing methods include but are not limited to rotating shaft 10 and thereby rotating bristles 21, proximal movement of the shaft 10, distal movement of the shaft 10, or any combination of these movements. While the bristles 21 are dislodging material from the interior of the vessel, the bristles 21 are also capturing material by virtue of their hook-like shape. When the lesion site has been suitably treated, the shaft 10 is removed from the patient's vasculature. If the procedure is deemed complete, the entire device will be disposed of. If further treatment is necessary, the bristles 21 can be cleaned by a thorough washing in sterile saline or urokinase and the entire process repeated.

If bristles 21 are made of a shape memory material, the shape memory properties of the bristles 21 can be used during the cleaning process. The preferred method is to use a two way shape memory alloy where bristles 21 assume a curved shape at body temperature. When the device is cleaned, the bristles 21 are washed in a sterile saline solution having a temperature corresponding to the temperature necessary to cause the bristles 21 to change to their memorized straight shape. Preferably, this transition temperature would be greater than any temperature that the device might encounter in use or storage, e.g. 45 Celsius (C). The straight bristles 21, then more easily release entrapped material. If a second use of the device is desired, the straight bristles 21 may be rinsed with sterile saline having a temperature below the transition temperature or simply allowed to cool below the transition temperature. This cooling causes the bristles 21 to return to their memorized curved shape in preparation for another use.

If bristles 21 are made of a one way shape memory alloy, the bristles 21 are used in their original curved shape. Similar to the method above, the bristles 21 are washed in a sterile saline solution having a temperature corresponding to the temperature necessary to cause the bristles 21 to change to their memorized straight shape, but greater than any temperature that the device might encounter in use or storage, preferably 45 C. However, cooling will not cause the bristles 21 to return to a curved shape. If a second use were necessary with bristles made of a one way shape memory alloy, the bristles could be bent back into curves prior to the second use.

Bending of bristles made of a one way shape memory alloy can be accomplished simply by bending them by hand or by using a bending tool. A bending tool may consist of a tube with very stiff fingers on the interior. The fingers are cut to a length such that when the distal end of the device is inserted into the bending tool and rotated the ends of the bristles of the device are bent over.

Figure 1C:
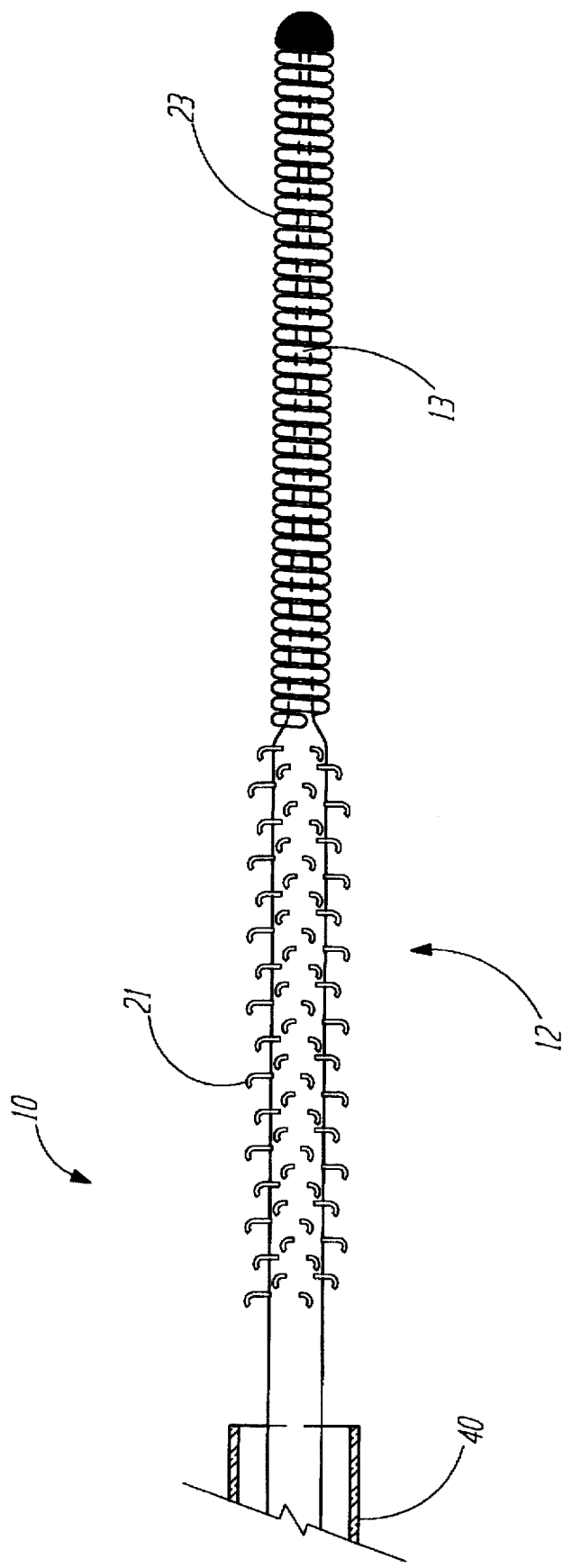
FIG. 1c is a side view of the embodiment of FIG. 1b with the sheath in a retracted position.

In FIGS. 1b and 1c a tubular sheath 40, of polyimide, polyethylene, Teflon™ or some other suitable medical grade polymer, surrounds both the proximal segment of shaft 10 and intermediate segment 12 of shaft 10. Sheath 40 has a wall thickness of about 0.001–0.004" and is sized such that it can easily be pulled back to expose bristles 21.

Use of the embodiment of FIGS. 1b and 1c may include inserting shaft 10 into a human's vasculature with the sheath 40 in its distal-most position, i.e., sheath 40 positioned such that it covers bristles 21, as in FIG. 1b. Once the bristles 21 are adjacent the site to be treated, the sheath 40 may be retracted to expose the bristles 21 to the patient's vasculature. Similarly to the embodiment shown in FIG. 1a, the bristles 21 are rotated or rubbed against the lesion in any way that will cause material to be dislodged from the interior of the vessel. However, this embodiment also allows the bristles 21 and the sheath 40 to work together to capture material.

Sheath 40 may be moved distally while bristles 21 are in contact with the lesion, thereby acting as a cutting edge. Additionally, sheath 40, in its distal-most position, may further insure that bristles 21 will hold the captured material while the shaft 10 is removed from the patient's vasculature. As in the embodiment of FIG. 1a, the device may be cleaned by washing it with sterile saline and reused, or the device can be discarded if the procedure is complete.

Figure 2:
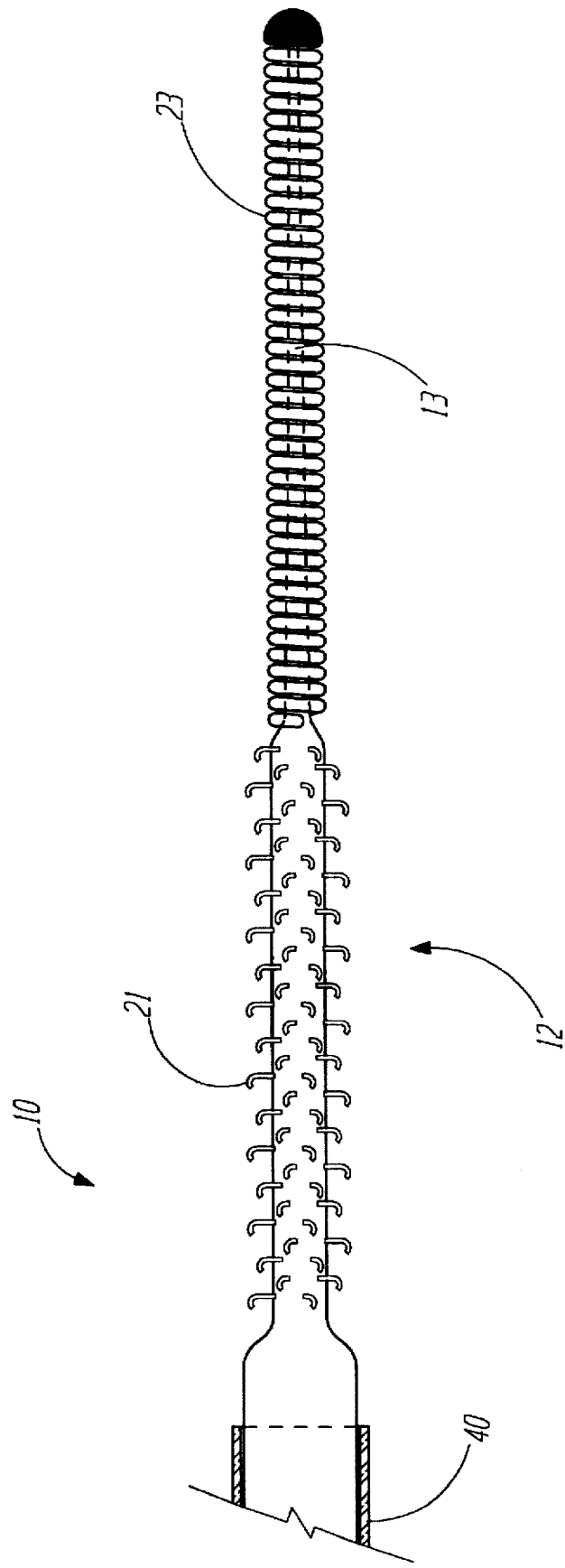
FIG. 2 is a side view of a modification of the embodiment of FIG. 1b including a segment having a reduced diameter.

FIG. 2 shows another embodiment wherein an intermediate segment 12 has been further ground to produce a segment with a smaller diameter than the proximal segment of shaft 10. This embodiment would be desirable for longer bristles 21 since there is greater clearance between the intermediate segment 12 and the sheath 40. Another possibility is that the originally disclosed length of bristles 21 would be used and more occlusive material could be captured when sheath 40 is returned to its distal-most position. Irrespective of the size of the bristles 21, this embodiment would have the added benefit of being able to capture more occlusive material while maintaining the same profile.

Figure 3:
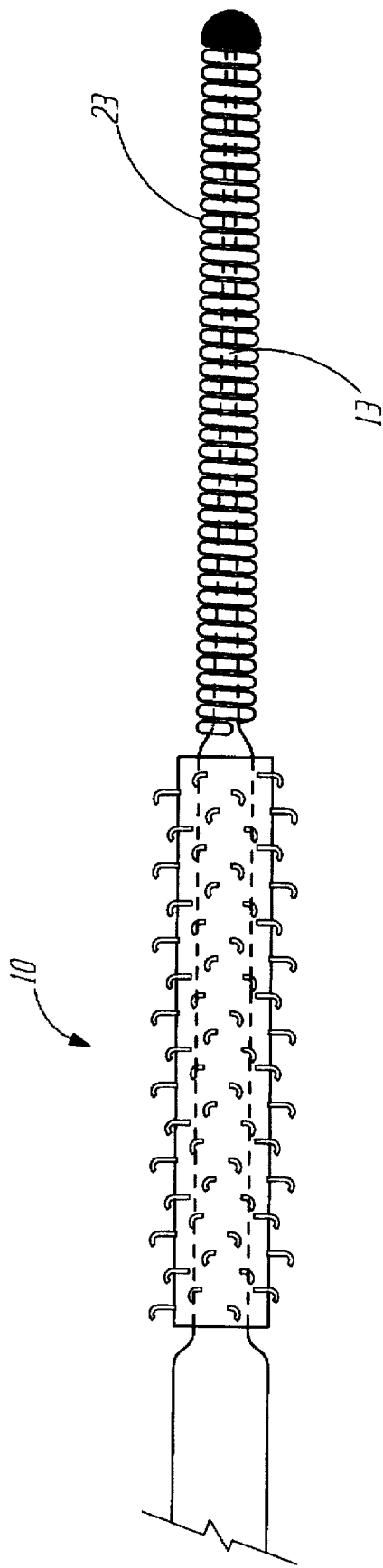
FIG. 3 is a side view of a second embodiment of the invention having an extended tapered distal segment surrounded by a sleeve.

FIG. 3 shows an embodiment of the invention having an extended distal segment 13 surrounded by a sleeve 22 made a suitable medical grade polymer. The proximal end of sleeve 22 is bonded to shaft 10 at the point where shaft 10 begins to taper into distal segment 13. Sleeve 22 has bristles 21 extending from its exterior. Although FIG. 3 shows the device without a sheath, a sheath could easily be added as previously described.

The embodiments shown in FIGS. 2 and 3 are used in the same ways as the embodiments shown in FIGS. 1a, 1b, and 1c.

Figure 4A:
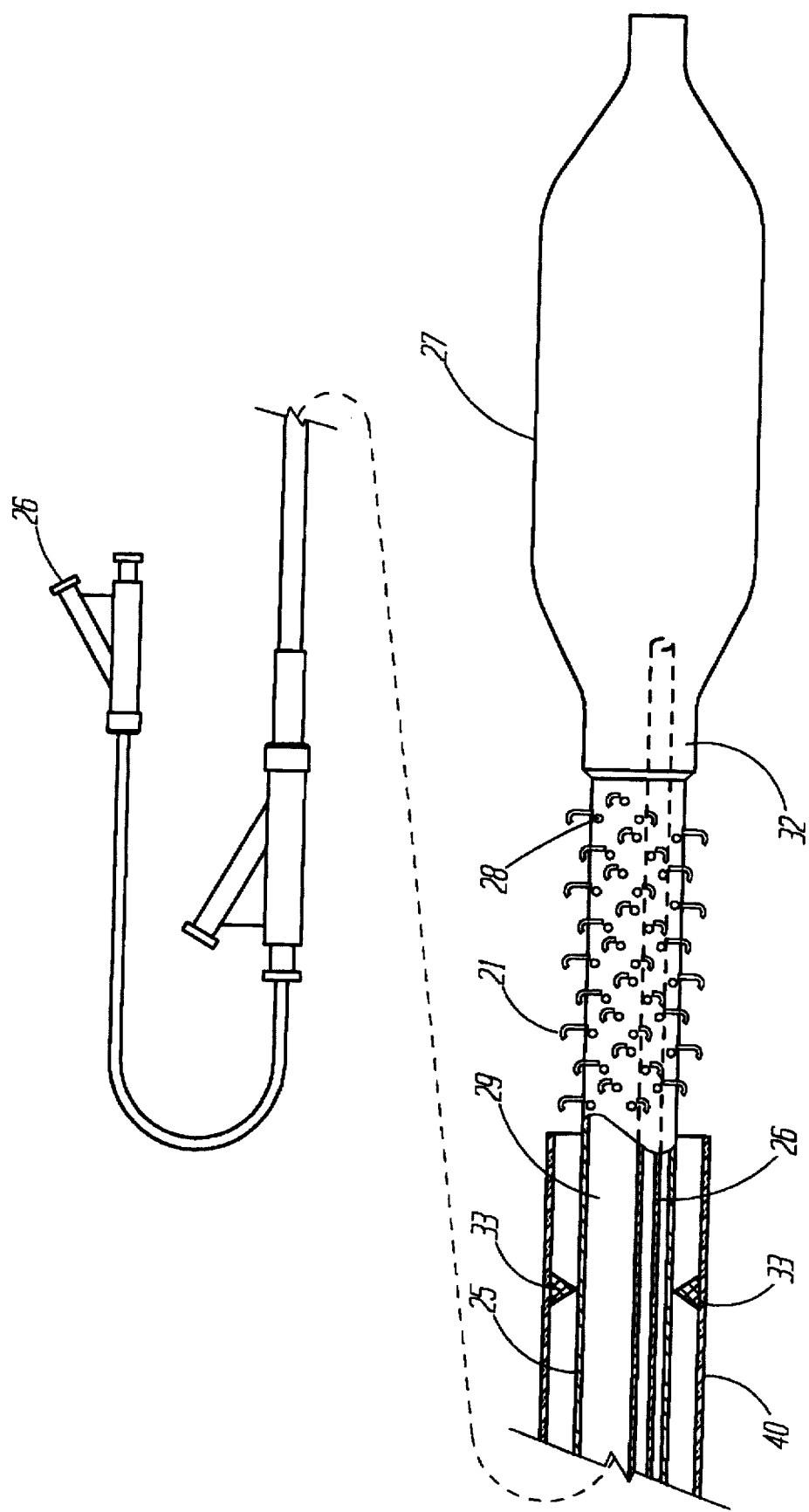
FIG. 4a is a side view of a third embodiment of the invention.
Figure 4B:
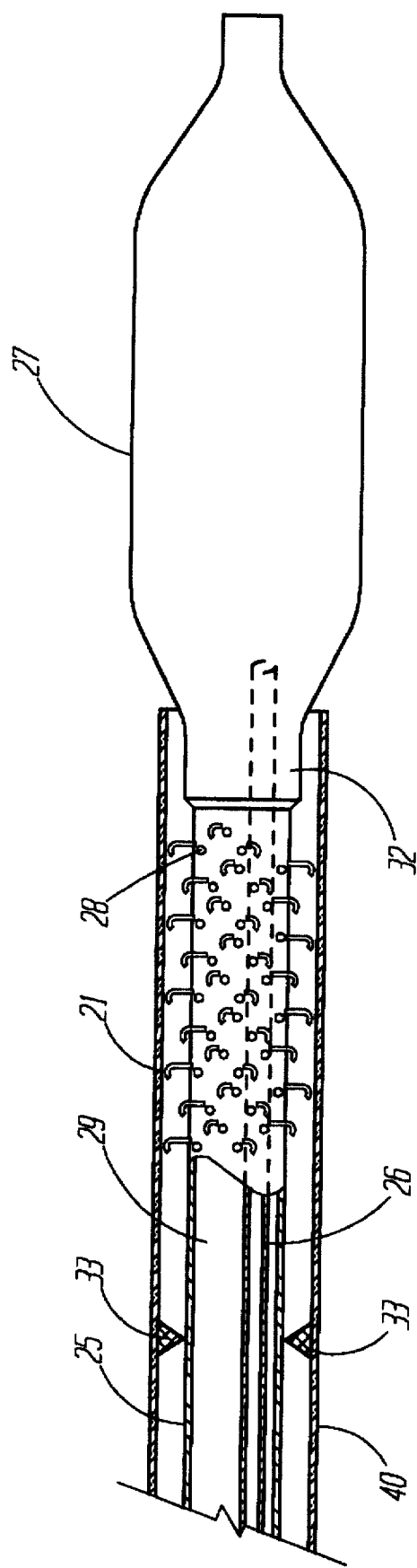
FIG. 4b is a side view of the embodiment of FIG. 4a including the sheath in a retracted position.

FIG. 4a and 4b shows another embodiment of the invention having a tube 25 made preferably of copolymer or stainless steel, Nitinol™, or any other suitable medical grade polymer. Tube 25 preferably has a diameter of 1–3 French (Fr). Within tube 25 there is a lumen 29 and a tube 26. Lumen 29 creates a fluid communication lumen between the proximal end of tube 25 and holes 28.

Tube 26 can be formed as a part of tube 25 or as a separate tube made of polyimide or any suitable medical grade polymer. Tube 26 is 1.0–1.5 Fr and creates a fluid communicating lumen between the proximal/end of tube 25 and a distal balloon 27. Balloon 27 is made of typical balloon materials such as POC, polyethylene, nylon, polyether block amide or polyethylene terephthaate. These materials allow balloon 27 to be made in compliant, semi-compliant, or non-compliant form. Balloon 27 has an inflated diameter larger than sheath 40, preferably 1.5–3.0 mm. Balloon 27 is bonded to the distal end of tube 25 at 32 with a suitable medical grade cyanoacrylate adhesive.

Sheath 40 has all of the structure and features of the previously described sheaths. In addition, sheath 40 has a restriction vent 33. Vent 33 is a cimumferential ring that can be adhesively bonded or preferably thermal formed on the interior of sheath 40. Vent 33 is shaped so as to restrict, but not stop, flow between the sheath 40 and the tube 25. This area of restricted flow forms a venturi effect that will accelerate any fluid flowing between the sheath 40 and the tube 25. When fluid flows through vent 33 it is accelerated to a speed that causes the flow to change from laminar to turbulent flow. Thus thrombus carried by this flow is shredded when the flow changes to a turbulent state.

Tube 25 has, at least of one radial hole 28 and a maximum of one hole 28 for each bristle 21, located proximal of balloon. 27. Holes 28 can be 0.001–0.010" in diameter and preferably will be spaced about 1.0 mm apart. Holes 28 allow fluid to pass from the interior of tube 25 to the exterior of tube 25. Tube 25 also has curved bristles 21, as previously described, located proximal of balloon 27.

FIGS. 4a and 4b show tube 25 without a guide wire. However, this device could also incorporate a guide wire either by use of an o-ring in the distal end of tube 25, a separate guide wire lumen, or in a fixed wire configuration.

In use, the embodiment portrayed in FIGS. 4a and 4b is inserted into a human's vasculature and advanced to the site to be treated. Once the bristles 21 are adjacent the area to be treated, the bristles 21 are rubbed against the lesion in any way that will cause material to be dislodged from the interior of the vessel. While the bristles 21 are dislodging material from the interior of the vessel, the bristles 21 are also capturing material by virtue of their hook-like structure. When the site has been suitably treated, this embodiment has the added advantage of being able to be cleaned in-vivo.

Sheath 40 is to the point where it contacts covers bristles 21. Balloon 27 is inflated through tube 26 to a pressure, preferably 17 atm (200 psi), suitable to seal bristles 21 between balloon 27 and sheath 40. A high pressure syringe or hand pump is attached to the proximal end of tube 25 and a fluid, such as, saline, contrast media, or other lysine agent, is pumped into tube 25. The fluid is pumped into tube 25 at a pressure, preferably about 200 psi, suitable to cause a venturi effect fluid velocity, at vent 33, and thereby great enough to cause turbulent flow downstream of vent 33. The fluid jets out of holes 28, cleans bristles 21, and carries any material trapped in bristles 21 back through the space between sheath 40 and tube 25. As the fluid flow passes through vent 33 it becomes turbulent, thereby causing shredding of any soft material cleaned from bristles 21. Clean bristles 21 will then be apparent when the refluxed fluid becomes clear or through angiographic inspection. When the fluid is clear, the balloon is deflated and the sheath retracted, providing a clean device prepared for further treatment.

While the specification describes the preferred designs, materials, methods of manufacture and methods of use, those skilled in the art will appreciate the scope and spirit of the invention with reference to the appended claims.

I claim:

1. A medical device for removing occlusive material and the like from a patient's vasculature or body cavities, the device comprising:

an elongate flexible shaft having a proximal end and a distal end, the distal end being insertable into the vasculature; and a plurality of flexible bristles disposed on the distal end of the elongate shaft, wherein the bristles comprise a shape memory material that reversibly changes shape when subjected to a change in temperature beyond a transition temperature and the bristles are adapted to capture occlusive material.

2. The medical device of claim 1, further comprising:

a retractable sheath disposed about the bristles.

3. The medical device of claim 1, further comprising:

an atraumatic tip attached to the distal end of the elongate shaft.

4. A method of removing occlusive material from a patient's vasculature, comprising the steps of:

providing an elongate shaft having a distal end and a plurality of shape memory bristles disposed about the distal end;

inserting the elongate shaft into the patient's vasculature;

capturing occlusive material in the bristles by moving the shaft through the occlusive material;

removing the elongate shaft and captured occlusive material from the patient's vasculature;

washing the occlusive material filled bristles in a liquid having a temperature suitable for changing the bristles from a memorized curved shape to a memorized straight shape; and cooling the straightened bristles to a temperature suitable for changing the shape memory material from the memorized straight shape to the memorized curved shape.

5. The method of claim 4 wherein the shaft includes a retractable sheath thereon, further comprising the step of:

retracting the sheath after inserting the elongate shaft into the patient's vasculature thereby allowing occlusive material to be captured in the bristles.

6. The method of claim 5 further comprising the steps of:

moving the sheath to its distal-most position following occlusive material capture, thereby further trapped occlusive material between the sheath and the bristles.

7. The method of claim 5, further comprising the step of:

moving the sheath distally so that the sheath acts as a cutter.

8. The method of claim 4 further comprising the steps of:

washing the occlusive material filled bristles in a liquid having a temperature suitable for changing a shape memory material from a memorized curved shape to a memorized straight shape; and bending the bristles back into a curved shape without cooling the straightened bristles.

9. A medical device comprising:

an elongate tube having a proximal end and a distal end, a first inflation lumen and a second flushing lumen extending therethrough, and a retractable sheath movably disposed about the elongate tube, the sheath having an interior;

an inflatable balloon attached to the distal end of the elongate tube and in fluid communication with the proximal end of the elongate tube via the first inflation lumen, the inflatable balloon having a smooth exterior suitable for sealing engagement with the distal end of the retractable sheath when the retractable sheath is moved over the balloon and the balloon is inflated;

a plurality of bristles disposed about the distal end of the elongate tube proximal of the balloon; and an at least one orifice in fluid communication with the second lumen and disposed adjacent the bristles.

10. The medical device of claim 9 further comprising:

a restriction vent disposed about the interior of the sheath.

11. The medical device of claim 9 wherein the elongate shaft has a guide wire lumen.

12. The medical device of claim 9 further comprising:

a stiffening wire disposed within the elongate tube.

13. A method of removing thrombus from a patient's vasculature comprising the steps of:

providing a catheter having a distal end, a balloon attached to the distal end, a plurality of bristles disposed about the catheter proximal of the balloon, and a retractable sheath disposed about the catheter;

inserting the catheter, into a patient's vasculature;

capturing occlusive material in the bristles;

moving the sheath over the curved bristles;

inflating the balloon, thereby sealing the bristles between the sheath and the catheter;

flushing a lysing fluid from within the catheter, over the bristles, and back out between the catheter and the sheath;

retracting the sheath;

capturing additional occlusive material; and removing the catheter from the patient's body.

* * * * *

UNITED STATES PATENT AND TRADEMARK OFFICE
CERTIFICATE OF CORRECTION

PATENT NO. : 5,702,413
DATED : December 30, 1997
INVENTOR(S) : LAFONTAINE

It is certified that error appears in the above-identified patent and that said Letters Patent is hereby corrected as shown below:

At column 2, line 18, "atherectomy thrombectomy should be --atherectomy/thrombectomy--

At column 3, line 52, "Wade" should be --grade--; at line 63, "Wade" should be --grade--.

At column 6, line 17, "proximal/end" should be --proximal end--; at line 20, "terephthaate" should be --terephthalate--; at line 28, "cimumferential" should be --circumferential--

At column 7, claim 1, line 6, "distal" should not begin a new paragraph.

Signed and Sealed this

Ninth Day of March, 1999

Attest:

Q. TODD DICKINSON

Attesting Officer

Acting Commissioner of Patents and Trademarks